(12) United States Patent
Tong

(10) Patent No.: US 8,691,994 B2
(45) Date of Patent: Apr. 8, 2014

(54) MULTI-COMPONENT POLYMERIZATION INHIBITORS FOR ETHYLENICALLY UNSATURATED MONOMERS

(75) Inventor: David Youdong Tong, Houston, TX (US)

(73) Assignee: Nalco Company, Naperville, IL (US)

( * ) Notice: Subject to any disclaimer, the term of this patent is extended or adjusted under 35 U.S.C. 154(b) by 381 days.

(21) Appl. No.: 13/020,487

(22) Filed: Feb. 3, 2011

(65) Prior Publication Data

US 2012/0203020 A1    Aug. 9, 2012

(51) Int. Cl.
*C07D 211/18*    (2006.01)
*C07C 11/00*    (2006.01)

(52) U.S. Cl.
USPC ............... 546/248; 526/82; 526/335

(58) Field of Classification Search
USPC .................................. 526/82, 335
See application file for complete search history.

(56) References Cited

U.S. PATENT DOCUMENTS

| | | | |
|---|---|---|---|
| 3,744,988 A | 7/1973 | Krumkalns et al. |
| 3,959,358 A | 5/1976 | Jursich |
| 4,670,131 A | 6/1987 | Ferrell |
| 4,720,566 A | 1/1988 | Martin |
| 5,290,888 A | 3/1994 | Gatechair et al. |
| 5,322,960 A | 6/1994 | Sakamoto et al. |
| 5,489,720 A | 2/1996 | Arhancet |
| 5,728,872 A | 3/1998 | Reimenschneider |
| 5,955,643 A | 9/1999 | Lewis |
| 6,262,323 B1 | 7/2001 | Elder |
| 6,300,513 B2 | 10/2001 | Sakamoto et al. |
| 6,337,426 B1 | 1/2002 | Winter |
| 6,342,647 B1 | 1/2002 | Roof et al. |
| 6,447,649 B1 * | 9/2002 | Arhancet .......................... 203/8 |
| 6,525,146 B1 * | 2/2003 | Shahid ............................ 526/82 |
| 6,579,442 B2 | 6/2003 | Eldin |
| 6,608,226 B1 | 8/2003 | Reid et al. |
| 6,627,766 B2 | 9/2003 | Reid et al. |
| 7,651,635 B1 | 1/2010 | Lewis |
| 2003/0105249 A1 | 6/2003 | Shahid |
| 2004/0132930 A1 | 7/2004 | Bonardi et al. |

FOREIGN PATENT DOCUMENTS

| | | |
|---|---|---|
| CN | 86103840 A | 12/1987 |
| JP | 2002234858 A | 8/2002 |
| WO | WO 98/14416 A1 | 4/1998 |
| WO | WO 01/40404 A | 6/2001 |

\* cited by examiner

*Primary Examiner* — Kamal Saeed
*Assistant Examiner* — Janet L Coppins
(74) *Attorney, Agent, or Firm* — Benjamin E. Carlsen

(57) ABSTRACT

The invention provides a composition and a method of using the composition for inhibiting the unwanted polymerization of ethylenically unsaturated monomers. The composition is prepared by reducing a nitroxide stable free radical to its corresponding hydroxylamine through reaction with a dialkyl/aryl hydroxylamine and subsequent addition of a polymerization prevention component selected from phenolic antioxidants, phenylenediamine and phenylenediamine derivatives, or phenothiazine and phenothiazine derivatives targeted towards ethylenically unsaturated monomers. The conversion of the nitroxide by the dialkyl/aryl hydroxylamine is to prevent it or the polymerization prevention component from being "spent"by reaction with each other, impurities or any other incompatible components. This allows previously incompatible combinations to now work effectively. In fact, the combination is more efficacious as the combination exerts a synergy due to the presence of various polymerization prevention reagents. The composition is a synergistic combination of various polymerization inhibition compounds for the inhibition of the unwanted polymerization of ethylenically unsaturated monomers.

12 Claims, 2 Drawing Sheets

MULTI-COMPONENT POLYMERIZATION INHIBITORS FOR ETHYLENICALLY UNSATURATED MONOMERS

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to compositions of matter and methods of using them to inhibit unwanted polymerization reactions of ethylenically unsaturated monomers. Polymerization inhibitors are known to be useful in preventing or reducing the unwanted polymerization of ethylenically unsaturated monomers which are handled at various stages of chemical processes in their manufacture and usage. Particularly, this invention illustrates a composition of inhibitors and retarders and its use in unwanted polymerization inhibition in handling the ethylenically unsaturated monomers.

Two categories of compounds have been developed to prevent unwanted polymerization reactions, inhibitors and retarders. Inhibitors prevent polymerization reactions from occurring. Inhibitors however are consumed rapidly. In cases of emergency when for mechanical or other reasons more inhibitor cannot be added, previously added inhibitor will be rapidly consumed and the unwanted polymerization reactions will then rapidly recur. Retarders slow down the rate of polymerization reactions but are not as effective as inhibitors. Retarders however are usually not consumed as quickly so they are more reliable in cases of emergency.

Ethylenically unsaturated monomers are reactive by their nature and they tend to polymerize through a radical polymerization mechanism. Unwanted polymerization reactions often impose operational concerns or difficulties while handling the ethylenically unsaturated monomers because the polymer formation may result in fouling and potential shutdown of operation equipment. Such is the case with the manufacture, transportation and storage of the monomers. It is especially a serious operational problem when distillation operation is involved in the manufacture and recovery of ethylenically unsaturated monomers, in which elevated operational temperatures accelerate the polymerization reactions of the monomers. Acrylonitrile is used as an example illustrating the handling of ethylenically unsaturated monomers, but not limited to, the manufacturing process described below.

The manufacture of acrylonitrile typically comprises three stages: the reaction, the recovery, and the purification stages. In the reaction stage, propylene, oxygen or air and ammonia are fed to a fluidized catalytic reactor. In the reactor, propylene undergoes a catalytic ammoxidation reaction to form acrylonitrile by reaction with ammonia and oxygen at an elevated temperature. The resulting acrylonitrile-containing reactor effluent is then cooled down in an aqueous quench column. In the quench column, unreacted ammonia is removed as ammonium sulfate by neutralizing with sulfuric acid. In the recovery stage the quench column overhead acrylonitrile-containing effluent undergoes a water absorption process in an absorber column to capture acrylonitrile and to dispose volatile components in the stream. Then, the effluent proceeds to a recovery column in which acrylonitrile is recovered through the overhead of the recovery column as an azeotropic distillate with hydrogen cyanide and water. This overhead distillate is then passed on to the purification stage.

In the purification stage, there are three sorts of equipment that are conventionally used in this sequence. First, a Heads Column is used to recover hydrogen cyanide from the feed. Second, a Drying Column dehydrates the acrylonitrile. Third, a Product Column yields the acrylonitrile product. In the Heads Column, hydrogen cyanide is separated as an overhead distillate through a conventional distillation operation. The bottom of the Heads Column is sent to a decanter for water removal. The organic phase of this decanter is routed to the Drying Column for further dehydration through an azeotropic distillation operation. The Drying Column overhead distillate is recycled back to the Heads Column, and the Drying Column bottoms are delivered to Product Column. In the Product Column heavy and light impurities are removed and a commercial grade of acrylonitrile is obtained as product. As with typical distillation operations, heating and elevated temperatures are involved in the Heads, Drying and Product column operations.

As one of the ethylenically unsaturated monomers, acrylonitrile tends to polymerize, and the polymerization reaction intensifies at elevated temperatures. Polymerization of acrylonitrile is unwanted in acrylonitrile manufacture since the resulting polymer tends to precipitate out of process stream, depositing on process equipment surfaces, and impairs the operation of the equipment. Acrylonitrile polymerization related fouling is often an operational concern for manufacturing and processing acrylonitrile, and it is especially a serious problem in the recovery and purification stages in acrylonitrile manufacture. Polymerization inhibitors have to be used routinely by acrylonitrile producers to mitigate polymerization induced fouling in process equipment or to stabilize acrylonitrile during transportation and storage. Nitroxide stable free radicals and hydroquinone (HQ) have been used to address these polymerizations.

HQ by itself is a less than optimal solution for unwanted polymerizations. As a polymerization inhibitor, HQ is only partially effective in inhibiting these polymerization reactions. Furthermore, HQ is a toxic chemical with environmental concerns.

Nitroxide stable free radicals, nitroxide hydroxylamines, N,N'-dialkyl/aryl substituted hydroxylamines, phenolic antioxidants, phenylenediamines and phenothiazines are well known reagents in the prevention of unwanted polymerization of ethylenically unsaturated monomers. The use of nitroxide stable radicals as polymerization inhibitors for ethylenically unsaturated monomers is mentioned for example in U.S. Pat. No. 3,744,988 which discusses the use of nitroxides, such as HTMPO in the inhibition of unwanted polymerization and resultant fouling in acrylonitrile manufacture. U.S. Pat. No. 4,670,131 discloses the use of stable free radicals, such as nitroxide, to inhibit polymerization of olefinic compounds.

Nitroxides are generally known as the most effective inhibitors owing to their superior inhibiting capability. Kinetically they are capable of scavenging carbon-centered free radicals at a nearly diffusion-controlled rate which is several orders of magnitude faster than phenolic compounds. However, their kinetic superiority is not always advantageous under certain circumstances. One issue of concern is their fast consumption rate as inhibitors. Other issues of concern are their consumption through non-inhibition, and their unwanted reactions with process stream components or other inhibitor additives. As a result, high nitroxide inhibitor dosages are often required for a given inhibition efficacy thereby making their use economically unattractive or even infeasible. Even worse, their interference with other inhibitors often results in antagonism and outright ineffectiveness as inhibitors.

U.S. Pat. No. 5,290,888 discloses the use of a N-hydroxy substituted hindered amine, such as 1,4-dihydroxy-2,2,6,6-tertamethylpiperidine, to stabilize ethylenically unsaturated monomers or oligomers from premature polymerization. N-hydroxy substituted hindered amines are usually prepared by reducing the corresponding nitroxide stable free radicals with a reducing reagent. N-hydroxy substituted hindered amines are excellent hydrogen donor due to the weak NO—H bond in the compounds, and thus they are efficient antioxidants. As antioxidants they react with peroxide radicals easily, while they are converted to their corresponding nitroxide. In essence, each N-hydroxy substituted hindered amine is equivalent to one hydrogen donor and one nitroxide inhibitor when peroxyl radicals and carbon-centered radicals are co-present, which is an attractive incentive offered by N-hydroxy substituted hindered amines. However, N-hydroxy substituted hindered amines are not stable when exposed to an oxygen-containing environment, such as storage in open air, as they are easily and gradually oxidized back to their corresponding nitroxide radicals.

One attempt to improve nitroxide inhibitors has been through the combination with other additives. When effective, these combinations are generally attributed to the combination of the fast kinetics of nitroxides in scavenging carbon-centered radicals and the durable action of other inhibitors or retarders in quenching carbon-centered and/or peroxyl radicals. Chinese patent application 86-1-03840 discloses a combined use of HTMPO and MEHQ in inhibiting the premature polymerization of methacrylic acid and isobutyric acid and its esters, but this requires the presence of oxygen. U.S. Pat. No. 5,728,872 discloses a combination of a nitroxide stable free radical, such as HTMPO, with a dihetero-substituted benzene having at least one transferable hydrogen, such as MEHQ, in inhibiting the premature polymerization of acrylic acid during the distillation process, either with or without the presence of oxygen. U.S. Pat. No. 5,955,643 discusses the use of a combination of nitroxide and phenylenediamine to inhibit the premature polymerization of vinyl aromatic monomers, such as styrene. U.S. Pat. No. 6,337,426 discusses a combination use of phenylenediamine and nitroxide to inhibit the premature polymerization of reactive light olefins, such as butadiene. U.S. Pat. No. 6,447,649 teaches the combined use of nitroxides and aliphatic amines to inhibit premature polymerization of vinyl monomers under both process and storage conditions. Examples of aliphatic amines are ethylenediamine, butane-1,4-diamine and propylamine.

Published PCT Application WO1998014416A1 teaches the combined use of a nitroxide and an oxime compound to inhibit the premature polymerization of vinyl aromatic monomers, such as styrene. U.S. Pat. No. 6,525,146 teaches the combined use of a hindered or unhindered phenol and an additional component selected from a nitroxide, a hydroxylamine, or a second different hindered or unhindered phenol to inhibit the premature polymerization of a diene compound, such as butadiene. US Published Patent Application 2004/0132930 discusses the combined use of a nitroxide and a dialkylhydroxylamine as a short-stopper in an aqueous suspension polymerization of vinyl chloride or mixed with another vinyl monomer. U.S. Pat. No. 5,322,960 discloses the combined use of a nitroxide, phenol and phenothiazine compounds in the inhibition of premature polymerization of (meth)acrylic acid and their esters. U.S. Pat. No. 6,300,513 discloses the combined use of an N-oxyl compound, N-hydroxy-2,2,6,6-tetramethylpiperidine, and 2,2,6,6-tetramethylpiperidine to stabilize vinyl compounds during their transport and storage. N-oxyl compounds are effective stabilizers for vinyl compounds, but they are lost with time in vinyl compounds. The co-presence of all three in a vinyl compound significantly reduces the loss of N-oxyl compounds with time in the vinyl compound. As a result, while the prior art does teach that nitroxides can sometimes be combined with other inhibitors or retarders these combinations often suffer from compatibility and storage issues, and are only useful in a limited number of environmental conditions.

For at least these reasons, there is a clear utility and novelty in other effective methods and compositions utilizing nitroxides and other polymerization prevention reagents for inhibiting unwanted polymerizations. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists. Any and all patents, patent applications, and other references cited by this application are hereby incorporated by reference in their entirety.

BRIEF SUMMARY OF THE INVENTION

At least one embodiment of the invention is directed towards a method of inhibiting the unwanted polymerization of an ethylenically unsaturated monomer prone to polymerization. The method comprises the steps of: a) providing a nitroxide stable free radical solution having a solvent, b) adding a sufficient amount of dialkyl/aryl hydroxylamine to the solution to reduce the nitroxide into the nitroxide hydroxylamine, c) adding to the solution a polymerization prevention component, thereby forming an inhibiting composition, and d) adding the composition to a fluid containing ethylenically unsaturated monomers. The polymerization prevention component is one selected from the list consisting of phenolic antioxidants, phenylenediamine derivatives, phenothiazine derivatives, and any combination thereof. The polymerization prevention component is targeted towards ethylenically unsaturated monomers. The polymerization prevention component is an item that would otherwise react with the nitroxide stable free radical but for the conversion of the nitroxide into nitroxide hydroxylamine.

The nitroxide stable free radical may be a derivative of TMPO. The dialkyl/aryl hydroxylamine may be a dialkyl hydroxylamine and may be DEHA. The phenolic antioxidant may be HQ. If the antioxidant were to have reacted with the nitroxide at least one of the antioxidants or the nitroxides may have had a lower inhibiting capacity than if they were not so reacted. The phenolic antioxidant may be one selected from the list consisting of: MEHQ, BHT, TBC and any combination thereof. The phenylenediamine derivative may be one selected from the list consisting of phenylenediamine, N-substituted phenylenediamine, and N,N'-substituted phenylenediamine. The phenothiazine derivative may be selected from phenothiazine and substituted phenothiazines. The nitroxide stable free radical may be HTMPO, the dialkyl/aryl hydroxylamine may be DEHA and the phenolic antioxidant may be HQ. The ethylenically unsaturated monomer may be selected from the list consisting of: acrylonitrile, (meth)acrolein, acrylic acid, methacrylic acid, acrylate esters, such as butylacrylate, ethylacrylate and methyl methacrylate, ethylene, propylene, styrene, divinylbenzene, butadiene, isoprene, vinylacetate, vinylacohol, and any combination thereof.

At least one embodiment of the invention is directed towards a composition for inhibiting the unwanted polymerization of an ethylenically unsaturated monomer prone to polymerization. The composition is produced by: a) providing a nitroxide stable free radical solution having a solvent, b) adding a sufficient amount of dialkyl/aryl hydroxylamine to the solution to reduce the nitroxide into the nitroxide hydroxylamine, and c) adding to the solution a polymerization prevention component, thereby forming an inhibiting composition. The polymerization prevention component is one selected from the list consisting of: phenolic antioxidants, phenylenediamine derivatives, phenothiazine derivatives, and any combination thereof. The polymerization prevention component is targeted towards the ethylenically unsaturated monomer. The polymerization prevention component is an item that would otherwise react with the nitroxide stable free radical but for the conversion of the nitroxide into nitroxide hydroxylamine.

DETAILED DESCRIPTION OF THE INVENTION

Figure 1:
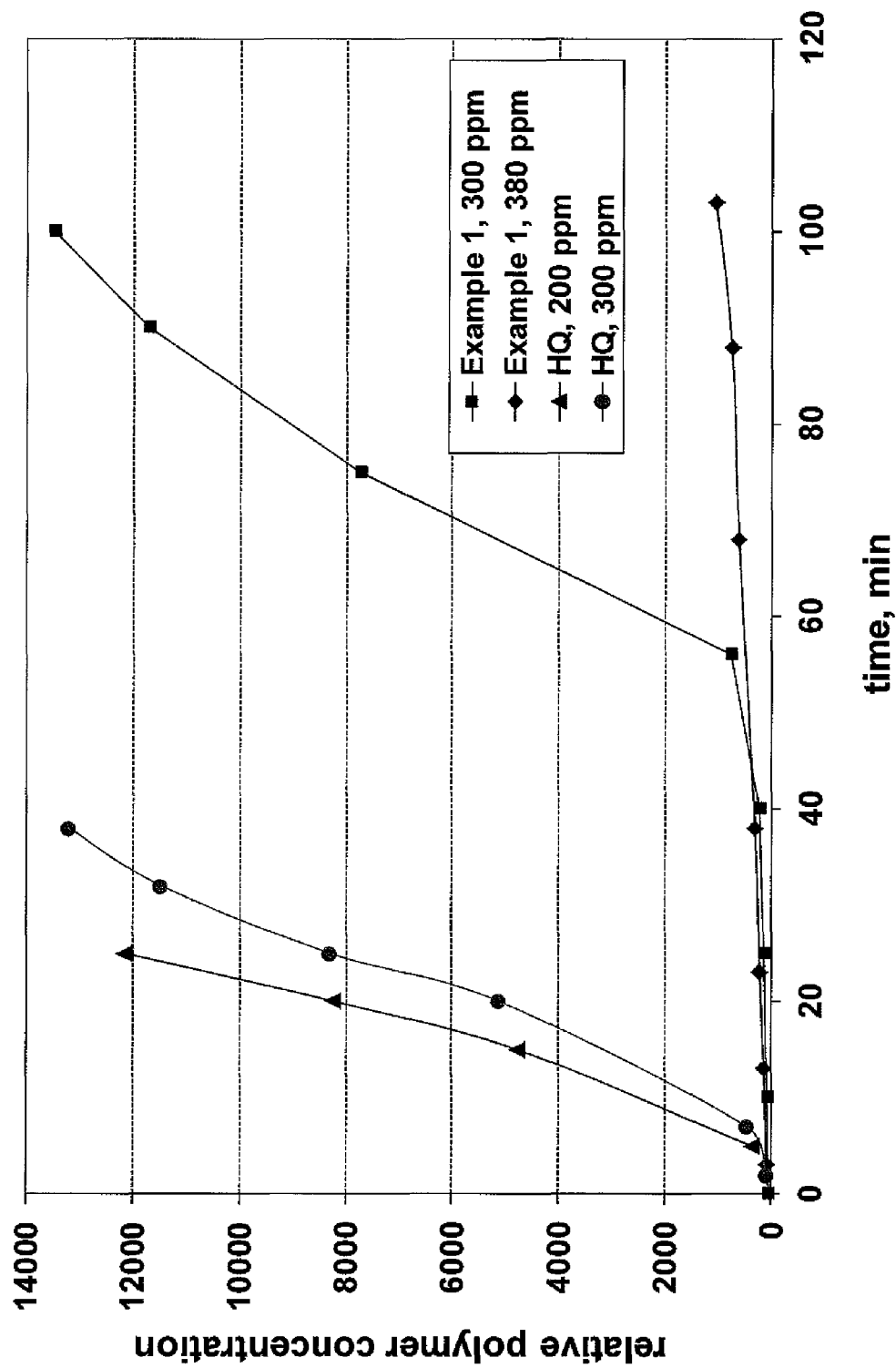
FIG. 1 is a graph illustrating the effectiveness of the invention at inhibiting the polymerization of pure acrylonitrile.

The following definitions are provided to determine how terms used in this application, and in particular how the claims, are to be construed. The organization of the definitions is for convenience only and is not intended to limit any of the definitions to any particular category.

"acrylate esters" means the esterification products of (meth)acrylic acid.

"BHT" means butylated hydroxytoluene.

"DEHA" means diethylhydroxylamine.

"HQ" means hydroquinone.

"HTMPO" means 4-hydroxy-2,2,6,6-tetramethylpiperidine-1-oxyl.

"Induction time" means the period of time in which in an ideal closed system a composition of matter completely prevents the formation of a particular polymer during a given reaction.

"Inhibitor" means a composition of matter that inhibits the formation of the particular polymer during an induction time but after the induction time has lapsed, the particular polymer's formation occurs at substantially the same rate that it would formed at in the absence of the composition of matter.

"MEHQ" means 4-methoxyphenol.

"(meth)acrolein" means both acrolein and methacrolein

"(meth)acrylic acid" means both acrylic acid and methacrylic acid

"PDA" means phenylenediamine.

"PTZ" means phenothiazine.

"Retarder" means a composition of matter, which does not have an induction time, but instead once added to the given reaction the composition of matter reduces the rate at which the formation of the particular polymer occurs relative to the rate at which it would have formed in the absence of the composition of matter.

"TBC" means 4-tert-butyl catechol.

"TMPO" means 2,2,6,6-tetramethylpiperidinal-1-oxyl

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology,* 5th Edition, (2005), (Published by Wiley, John & Sons, Inc.) this definition shall control how the term is to be defined in the claims.

In at least one embodiment an unwanted polymerization reaction of an ethylenically unsaturated monomer is prevented at the handling stage of the ethylenically unsaturated monomer by the presence of an effective amount of an inhibiting composition. The composition comprises:

1) a nitroxide stable free radical solution;
2) a sufficient amount of dialkyl/aryl hydroxylamine to convert effectively all of the nitroxide into nitroxide hydroxylamine; and
3) a polymerization prevention component selected from phenolic antioxidants, phenylenediamine derivatives, phenothiazine derivatives, targeted towards the ethylenically unsaturated monomer, the component being one that would otherwise react with the nitroxide stable free radical but for the conversion of the nitroxide into nitroxide hydroxylamine; and The composition as inhibitor can be added to the ethylenically unsaturated monomer and unwanted polymerization of the ethylenically unsaturated monomer is effectively inhibited.

In at least one embodiment the nitroxide stable free radical is a derivative of TMPO. HTMPO is an example of a TMPO derivative. Other TMPO derivatives include, but are not limited to 4-oxo-TMPO, 4-amino-TMPO, 4-acetate-TMPO, Bis-(2,2,6,6-tetramethylpiperidine-1-oxyl)sebacate, and any combination thereof.

In at least one embodiment the dialkyl/aryl hydroxylamine is a dialkyl or diaryl hydroxylamine. Examples are diethyl hydroxylamine (DEHA), dipropyl hydroxylamine, dibutyl hydroxylamine, bis-(hydroxypropyl)hydroxylamine (HPHA) and dibenzyl hydroxylamine.

In at least one embodiment the phenolic antioxidant is selected from hindered and nonhindered phenols targeted toward an ethylenically unsaturated monomer. Examples of such phenolic antioxidants are HQ, BHT, TBC, and MEHQ.

In at least one embodiment the phenylenediamine derivative is selected from an unsubstituted phenylenediamine, N-substituted phenylenediamine or N,N'-substituted phenylenediamine targeted towards an ethylenically unsaturated monomer, and any combination thereof. Examples of phenylenediamine derivatives are 1,4-phenylenediamine, N,N'-dimethyl-p-phenylenediamine, N, N'-di-sec-butyl-p-phenylenediamine, N-phenyl-N'-dibutyl-p-phenylenediamine, N-phenyl-N'-(1,4-dimethylphenyl)-p-phenylenediamine, N-phenyl-N'-(1,3-dimethylbutyl)-p-phenylenediamine, and any combination thereof.

In at least one embodiment the phenothiazine derivative is selected from PTZ and substituted PTZ targeted toward an ethylenically unsaturated monomer. Examples of substituted PTZ include alkylated PTZ.

In at least one embodiment the ethylenically unsaturated monomer is selected from the list of: acrylonitrile, (meth) acrolein, (meth)acrylic acid, acrylate ester, ethylene, propylene, styrene, divinylbenzene, butadiene, isoprene, vinyl acetate, vinyl alcohol and any combination thereof. Butyl acrylate, ethyl acrylate, methyl methacrylate are the examples of acrylate ester.

In at least one embodiment the solvent of the nitroxide stable free radical solution is selected from the list consisting of, but not limited to: water, alcohol, ether, ketone, ester, glycol, aliphatic and aromatic hydrocarbons, ethylenically unsaturated monomers and any combination thereof.

In at least one embodiment the polymerization prevention component is HQ and the targeted ethylenically unsaturated monomer is acrylonitrile, (meth)acrolein or (meth)acrylic acid.

In at least one embodiment the polymerization prevention component is TBC and the ethylenically unsaturated monomer is butadiene, isoprene, styrene, divinylbenzene, and/or acrylonitrile.

In at least one embodiment the polymerization prevention component is PTZ and the ethylenically unsaturated monomer is (meth)acrylic acid or acrylate ester.

In at least one embodiment the polymerization prevention component is PDA and the ethylenically unsaturated monomer is butadiene, isoprene, acrylonitrile, styrene, divinylbenzene, (meth)acrylic acid, and/or acrylate ester.

In at least one embodiment the polymerization prevention component is BHT and the ethylenically unsaturated monomer is ethylene, propylene, styrene, divinylbenzene, and/or acrylonitrile.

In at least one embodiment the polymerization prevention component is MEHQ and the ethylenically unsaturated monomer is acrylonitrile or (meth)acrolein or (meth)acrylic acid or acrylate esters, such as butylacrylate, ethylacrylate, methylmethacrylate.

In at least one embodiment the nitroxide is HTMPO, the dialkyl hydroxylamine is DEHA, the polymerization prevention component is HQ and the ethylenically unsaturated monomer is acrylonitrile.

Without being limited by theory and in particular to the construal of the claims, it is believed that the presence of the nitroxide group or the corresponding nitroxide hydroxylamines, dialkyl/aryl hydroxylamine or its corresponding nitrone and a component selected from phenolic antioxidant, phenylenediamine or phenothiazine targeted towards an ethylenically unsaturated monomer results in a synergistic combination that is more effective than merely the sum of their parts. This synergistic combination involves the nitroxide group acting as an antipolymerant (an inhibitor of the polymerization of carbon centered radicals), nitroxide hydroxylamine as an antioxidant (an inhibitor of peroxyl radicals) and also an in situ source for nitroxide antipolymerant, the dialkyl/aryl hydroxylamine as an antioxidant, the nitrone as an antipolymerant or antioxidant and the phenolic antioxidant, phenylenediamine or phenothiazine targeted towards a given ethylenically unsaturated monomer as an inhibitor or retarder. This synergistic combination provides not only a synergistic inhibition function mechanism (antioxidant vs. antipolymerant or inhibitor vs. retarder), but also a leveraged and comprehensive coverage in terms of inhibition kinetics, which ensures an instantaneous and long-lasting quench of both carbon and oxygen centered free radicals. Another advantage of this composition is the ease of delivery of this inhibitor package into an ethylenically unsaturated monomer handling system. Pre-formulations of this composition avoid the need for on-site blending and the associated safety and environmental concerns. Such a multi component blend reduces the expenses associated with additional injection points for multiple products.

While the prior art does teach the concurrent use of stable free radical antipolymerants and antioxidants/inhibitors/retarders, they are not as effective or efficient as the invention. Nitroxides, such as HTMPO, tend to react with process components or impurities or antioxidant/inhibitors/retarders, to form non-effective inhibitors and thus rapidly lose their effectiveness as antipolymerants. In this invention however, the reaction with the dialkyl/aryl hydroxylamine both preserves the effectiveness of the antipolymerant and prevents the antipolymerant from reacting into a spent nitroxide through reaction with other chemicals. This allows the nitroxide stable free radicals to be formulated and used with what would otherwise be incompatible antioxidants/inhibitors/retarders.

EXAMPLES

The foregoing may be better understood by reference to the following examples, which are presented for purposes of illustration and are not intended to limit the scope of the invention.

Example 1

Preparation of an Inhibitor Composition

An example inhibitor composition was prepared. HTMPO was dissolved in a solvent consisting of water, ether, and glycol. DEHA was then added into the solution. A discoloration was observed as the reaction between HTMPO and DEHA progressed. At the end of this reaction, compositional analysis confirmed the conversion of HTMPO to HTMPO hydroxylamine and the formation of a nitrone from DEHA. HQ was then added and dissolved with stirring. This composition was ready for use as an inhibitor product.

Example 2

Inhibitor Performance Test with Uninhibited Acrylonitrile

The performance of the above generated inhibitor composition was evaluated using a laboratory scale continuous flow distillation column. In this laboratory setup, the column consisted of a three-neck flask representing the column sump and reboiler, an insertion assembly with perforated metal plates representing the distillation column tray section, and a condenser representing the overhead condenser to provide distillation reflux. A feed pump provided the column feed, and an outlet purge pump maintained the liquid level in the sump. Heating was provided via a heating mantle to the flask contents.

Commercial grade acrylonitrile was purchased from Sigma-Aldrich (99+% pure, inhibited with 35-45 ppm MEHQ). Uninhibited acrylonitrile was obtained by removing the MEHQ. Benzoyl peroxide (BPO) (Aldrich, 97%) was employed as the polymerization initiator for the experiments.

Four individually treated runs were compared in FIG. 1 in terms of polymer concentration versus run time. The polymer concentration in the sump increased with time as a result of polymer formation. An effective inhibitor would be expected to reduce polymer formation in the distillation column and thus slow down the concentration rise of polymer in the sump. FIG. 1 shows that the inhibitor composition made in Example 1 effectively inhibits polymer formation in pure acrylonitrile with a significant dosage response while the two HQ treated runs show little inhibition.

Example 3

Figure 2:
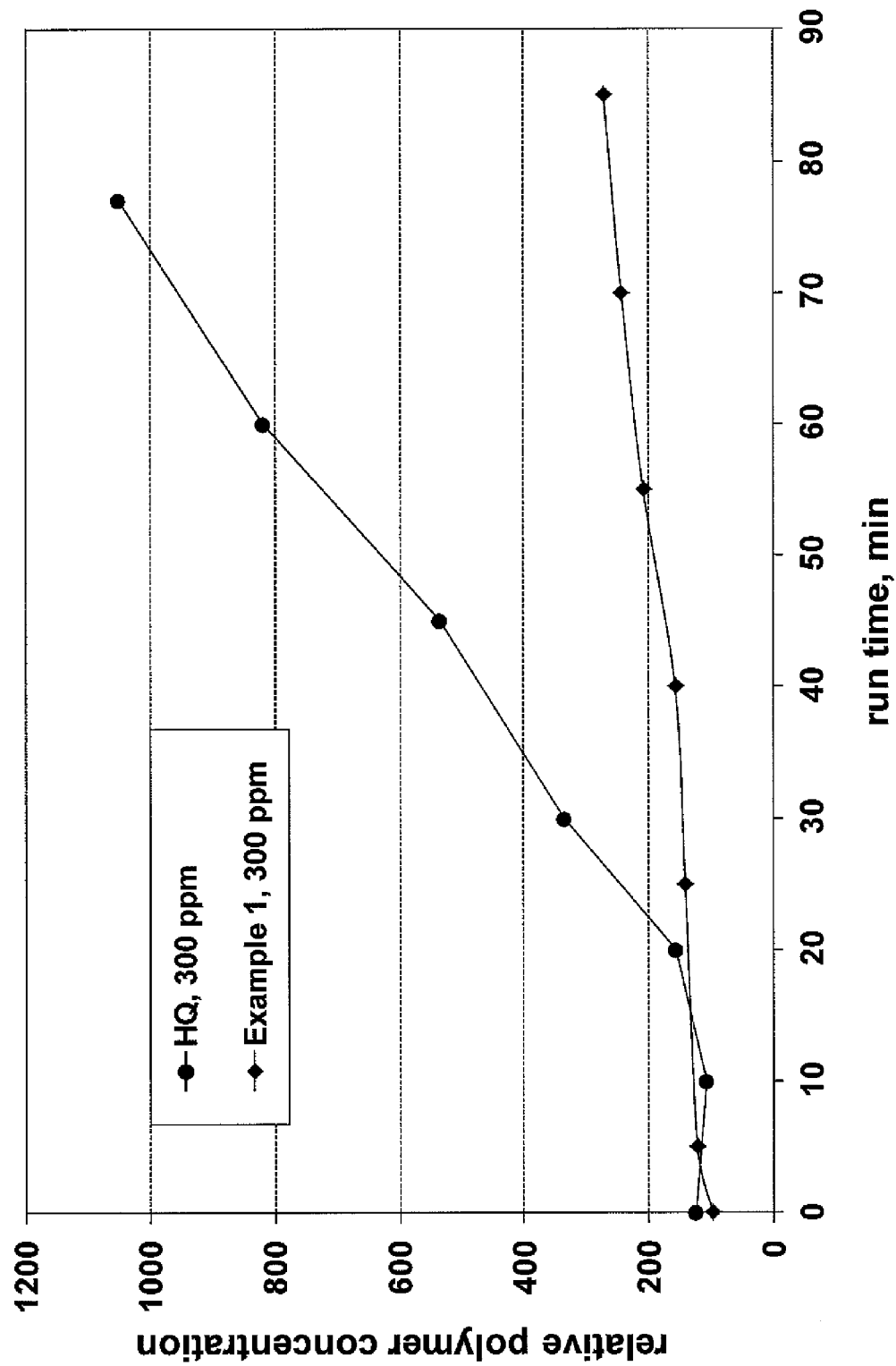
FIG. 2 is a graph illustrating the effectiveness of the invention at inhibiting the polymerization of acrylonitrile in the presence of water, acetic acid, and air.

Inhibitor Performance Test with the Presence of Acetic Acid, Water and Air in Uninhibited Acrylonitrile The data shown in FIG. 2 was collected using the same apparatus as in Example 2, except that acetic acid, water and air were introduced in the distillation column, to simulate the distillation operation in the Heads or Drying column of an industrial acrylonitrile manufacture process. FIG. 2 shows that in the presence of water, acetic acid, and air the HQ retarded acrylonitrile polymerization, while the Example 1 composition inhibited the polymerization up to 40 minutes and is mostly effective after 85 minutes have elapsed.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of inhibiting the unwanted polymerization of an ethylenically unsaturated monomer prone to polymerization, wherein the ethylenically unsaturated monomer is selected from a list of acrylonitrile, (meth)acrolein, (meth)acrylic acid, acrylate esters, butylacrylate, ethylacrylate, methyl methacrylate, ethylene, propylene, styrene, divinylbenzene, vinyl acetate, vinyl alcohol, and any combination thereof, the method comprising the steps of:
   a) providing a nitroxide stable free radical solution having a solvent;
   b) adding a sufficient amount of dialkyl/aryl hydroxylamine to the solution to reduce the nitroxide to the nitroxide hydroxylamine;
   c) adding to the solution a polymerization prevention component, thereby forming an inhibiting composition; and
   d) adding the composition to a fluid containing ethylenically unsaturated monomers;
   wherein the polymerization prevention component is one selected from the list consisting of phenolic antioxidants, phenylenediamine and phenylenediamine derivatives, phenothiazine and phenothiazine derivatives, and any combinations thereof, and the polymerization prevention component is targeted towards ethylenically unsaturated monomers, and the polymerization prevention component is an item that would otherwise react with the nitroxide stable free radical but for the conversion of the nitroxide into nitroxide hydroxylamine.

2. The method of claim 1 wherein the nitroxide stable free radical is a derivative of TMPO.

3. The method of claim 1 wherein the dialkyl/aryl hydroxylamine is a dialkyl hydroxylamine.

4. The method of claim 2 wherein the nitroxide stable free radical is HTMPO.

5. The method of claim 3 in which the dialkyl hydroxylamine is DEHA.

6. The method of claim 1 wherein the phenolic antioxidant is HQ.

7. The method of claim 1 wherein but for the presence of the polymerization prevention component the antioxidant would have reacted with the nitroxide and thereby at least one of the antioxidant or the nitroxide would have had a lower inhibiting capacity than if they were not so reacted.

8. The method of claim 1 wherein the phenolic antioxidant is one selected from the list consisting of: MEHQ, BHT, TBC and any combination thereof.

9. The method of claim 1 wherein the phenylenediamine and phenylenediamine derivative is one selected from the list consisting of phenylenediamine, N-substituted phenylenediamines, and N,N'-substituted phenylenediamines.

10. The method of claim 1 wherein the phenothiazine derivative is selected from phenothiazine and substituted phenothiazines.

11. The method of claim 1 wherein the nitroxide stable free radical is HTMPO, the dialkyl/aryl hydroxylamine is DEHA and the phenolic antioxidant is HQ.

12. A composition for inhibiting the unwanted polymerization of an ethylenically unsaturated monomer prone to polymerization, the composition produced by:
   a) providing a nitroxide stable free radical solution having a solvent;
   b) adding a sufficient amount of dialkyl/aryl hydroxylamine to the solution to reduce the nitroxide to the nitroxide hydroxylamine;
   c) adding to the solution a polymerization prevention component, thereby forming an inhibiting composition; and
   d) adding the composition to a liquid containing ethylenically unsaturated monomers;
   wherein the polymerization prevention component is one selected from the list consisting of phenolic antioxidants, phenylenediamine and phenylenediamine derivatives, phenothiazine and phenothiazine derivatives, and any combinations thereof, and the polymerization prevention component is targeted towards ethylenically unsaturated monomers, and the polymerization prevention component is an item that would otherwise react with the nitroxide stable free radical but for the conversion of the nitroxide into nitroxide hydroxylamine.

* * * * *

UNITED STATES PATENT AND TRADEMARK OFFICE
CERTIFICATE OF CORRECTION

PATENT NO.         : 8,691,994 B2                                          Page 1 of 1
APPLICATION NO.    : 13/020487
DATED              : April 8, 2014
INVENTOR(S)        : Youdong Tong It is certified that error appears in the above-identified patent and that said Letters Patent is hereby corrected as shown below:

In the Claims at column 10, line number 43 - remove "dialkyllaryl" and replace with "dialkyl/aryl".

Signed and Sealed this
Third Day of November, 2015

Michelle K. Lee
*Director of the United States Patent and Trademark Office*